United States Patent [19]

Berigari

[11] Patent Number: 5,595,914
[45] Date of Patent: Jan. 21, 1997

[54] GYPSUM DETERMINATION IN SOILS BY CONVERSION TO WATER-SOLUBLE SODIUM SULFATE

[76] Inventor: Mohammed S. Berigari, 10520 Oak Bluff Ct., Burke, Va. 22015

[21] Appl. No.: 547,013

[22] Filed: Oct. 23, 1995

[51] Int. Cl.$^6$ ............................................. G01N 1/00
[52] U.S. Cl. .............................. 436/177; 436/25; 436/31; 436/174
[58] Field of Search .................................. 436/174, 177, 436/25, 31

[56] References Cited

U.S. PATENT DOCUMENTS 4,504,458  3/1985  Knodsen ................................... 423/552

OTHER PUBLICATIONS

Saeed et al. "A Method for the Conversion of Gypsum into Sodium Sulfate"; Pak. J. Sci. Ind. Res. (1983), 26(4), 272–4.
Skaric, et al. "Sulfate and Gypsum Determination in Saline Salts". Soil Sci. Soc. Am. J., (1989), 51, 901–905.

Primary Examiner—Jill Warden
Assistant Examiner—Sharidan Carrillo
Attorney, Agent, or Firm—Robert Platt Bell & Associates, P.C.

[57] ABSTRACT

Precise and accurate determination of gypsum in soils has been difficult, laborious and time consuming by currently available methods. The present invention solves such problems by: 1) Direct removal of nongypsic sulfate from 2-g soil sample with 25-mL portion of 50-% (v/v) ethanol, thus, eliminating positive errors in gypsum measurement from sulfate analysis while causing essentially no loss in gypsum content of the sample, and 2) stoichiometric conversion of soil gypsum to $Na_2SO_4$ and $CaCO_3(s)$ by two equlibrations of the soil sediment with 25-mL increments of 0.5M $Na_2CO_3$ solution plus 30-s sonification. The $SO_4$ in the supernatent solution is centrifuge separated, analyzed by the standard $BaSO_4$ gravimetric and turbidimetric methods, and gypsum content is computed from equation [8]:

$$\text{gypsum(g)/soil(kg)} = [SO_4(g) \text{ /soil(kg)}(172/96.1)] \qquad [8]$$

2 Claims, No Drawings

GYPSUM DETERMINATION IN SOILS BY CONVERSION TO WATER-SOLUBLE SODIUM SULFATE

TECHNICAL FIELD

This invention relates to a novel method of gypsum determination in soil samples based on prior removal of nongypsic sulfates then stoichiometric conversion of soil gypsum to water soluble $Na_2SO_4$. Gypsum is determined from sulfate analysis in the soil-aqueous extract by standard $BaSO_4$ methods. The invented method is simple, precise, accurate and rapid for soil taxonomy, land reclamation, and other purposes.

DESCRIPTION OF THE PRIOR ART

Gypsiferous soils widely occur in arid and semi-arid regions. Complete extraction and accurate measurement of soil gypsum are often needed for soil taxonomy and land reclamation purposes. Skarie et al (1987) pointed out critical limitations of commonly used physical and chemical methods of gypsum determination in soils. Currently, the only conventional method available for gypsum determination in soils is that described by Nelson (1982) which is laborious and time consuming. Nelson's method is based on solubility of gypsum in water which is low (30 meq/liter) through preparation of a soil-water extract that is sufficiently dilute (10 meq/liter) to dissolve all gypsum present in the sample. Gypsum is then determined from sulfate analysis by standard methods. However, selection of water/soil ratio that provides gypsum concentration of 10 meq/liter for faster rate of its dissolution requires a time consuming trial and error method or semiquatitative determination of gypsum in the sample to reduce the time for such selection (see the attached photocopy of Nelson's method).

It is clear that Nelson's method (1982) for gypsum determination in soils is very laborious and time consuming, thus, the need for a simple, rapid, accurate and precise method is quite obvious.

References:
1. Nelson, R. E. 1982. Carbonate and gypsump. P. 181–197. In A. L. Page et al. (ed.) Methods of soil analysis. Part 2. 2nd ed. Agron. Monogr. 9. ASA and SSSA, Madison, Wis.
2. Skarie, R. L., J. L. Arndt, and J. L. Richardson. 1987. Sulfate and gypsum determination in saline soils. Soil Sci. Soc. Am. J. 51: 901–905.

SUMMARY OF THE INVENTION

The objective of this invention is to provide a simple, accurate, precise and rapid method of gypsum determination in soils. The invented method meets these criteria and requires limited means:

1. Centrifuge wash once a 2-g air-dried soil sample with 25-mL of 50% (v/v) ethanol in a 50-mL centrifuge tube to selectively remove nongypsic sulfates, thus, directly eliminate positive errors in gypsum measurement.
2. Convert completely soil gypsum to water-soluble sodium sulfate by two equilibrations of the soil sediment with 25-mL portions of 0.5M $Na_2CO_3$ solution plus 30-s sonification. Centrifuge separate the extract and analyze sulfate by standard $BaSO_4$ turbidimetry to compute gypsum content of the soil sample.

DETAILED DESCRIPTION OF THE INVENTION

The Method I am going to describe in details bears all the merits of an excellent standard procedure for gypsum determination in soils for soil taxonomy, land reclamation and other purposes. The method was developed by the present inventor (senior author) and published in the Soil Science Society of America Journal, Volume 58, no 6, November-December 1994, Page 1624–1627 (two copies of reprint are attached). Gypsum Determination in Soils by Conversion to Water-Soluble Sodium Sulfate.

Procedure:

Triplicate 2.0-g air-dry soil samples in 50-mL polycarbonate centrifuge tubes were washed once with 25-mL portions of 50% (v/v) ethanol plus 30-s sonification to remove soluble sulfate while reducing the solubility of gypsum to a negligible value (0.62 mg/2.0 g sample or 0.03% error). The bulk solution was centrifuged and the sediment was suspended in 25-mL of 0.50M $Na_2CO_3$ solution by a 30-s sonification to disturb formation of stable $CaCO_3(s)$ coating on soil gypsum, thus enhancing its stoichiometric conversion to the water soluble $Na_2SO_4$. The supernatent solution was centrifuge separated at 1000×g and 25° C., then filtered quantitatively through Whatman no. 42 filter paper. This extraction procedure was repeated once more or until a negative test for $SO_4$ with $BaCl_2$ crystals was obtained to ensure complete removal of gypsum from the sample. Sulfate in the aqueous extract was analyzed by the standard $BaSO_4$ gravimetry and turbidimetry after the necessary dilutions and acidifications to prevent precipitation of $BaCO_3(s)$ and $Ba_3(PO_4)_2$ (Greenberg et al. 1985). Also, the correction for sample color and turbidity was applied for turbidimetric sulfate measurement as described by Greenberg et al. (1985). Gypsum content of the soil sample was obtained from sulfate analysis assuming that all the $SO_4$ in the extract came from soil gypsum, $CaSO_4.2H_2O$ using Eq. [7].

$$\text{gypsum(g)/soil(kg)} = [SO_4(g)/\text{soil(kg)}] \cdot (172/96.1)]. \quad [7]$$

References:
1. Berigari, M. S., and F. M. Al. Any. 1994. Gypsum determination in soils by conversion to water-soluble sodium sulfate. Soil Sci. Soc. Am. J. 58:1624–1627.
2. Greenberg, A. E., R. R. Trussell, and L. S. Clesceri. 1985. Standard methods for the examination of water and wastewater. 16th ed. Am. Public Health Assoc., Washington, D.C.

I claim:

1. A method for selective removal of nongypsic sulfates from 2-gram soil samples comprising the steps of:
   a) adding each soil sample to a centrifuge tube:
   b) adding a 50% ethanol solution to each said soil samples contained in said centrifuge tube;
   c) sonificating each of said soil samples; and
   d) centrifuging each of said soil samples to remove said nongypsic sulfates, whereby substantially no gypsum is lost from each of said soil samples.

2. A method for complete conversion of gypsum in 2-gram soil samples to water-soluble sodium sulfate comprising the steps of:
   a) adding each soil sample to a centrifuge tube;
   b) adding a 50% ethanol solution to each of said soil samples contained in said centrifuge tube;
   c) sonificating each of said soil samples;
   d) centrifuging each of said soil samples to remove nongypsic sulfates;

e) adding a 25 milliliter aliquot of 0.5M $Na_2CO_3$ solution to each of said soil samples to form a water-soluble sodium sulfate solution;

f) sonificating each of said soil samples to form a water-soluble sodium sulfate solution;

g) centrifuging each of said soil samples; and h) separating the supernatant solution of each of said soil samples for sulfate analysis by $BaSO_4$.

* * * * *